United States Patent [19]

Meruelo et al.

[11] Patent Number: 5,506,271
[45] Date of Patent: Apr. 9, 1996

[54] METHOD OF TREATING PAPILLOMA VIRUS INFECTION USING HYPERICIN

[75] Inventors: Daniel Meruelo, Scarborough, N.Y.; Gad Lavie, Tenafly, N.J.

[73] Assignee: New York University, New York, N.Y.

[21] Appl. No.: 103,775

[22] Filed: Aug. 10, 1993

Related U.S. Application Data

[63] Continuation-in-part of Ser. No. 821,945, filed as PCT/US93/00364, Jan. 19, 1993, abandoned.

[51] Int. Cl.$^6$ .................... A61K 31/045; A61K 31/015
[52] U.S. Cl. .................... 514/732; 514/934; 514/969
[58] Field of Search .................... 514/732, 969, 514/934; 435/236

[56] References Cited

U.S. PATENT DOCUMENTS

| | | | |
|---|---|---|---|
| 4,898,891 | 2/1990 | Lavie et al. | 514/732 |
| 5,047,435 | 9/1991 | Lavie et al. | 514/732 |
| 5,182,104 | 1/1993 | Marcus et al. | 424/78.07 |
| 5,244,922 | 9/1993 | Burzylski | 514/561 |
| 5,316,768 | 5/1994 | Hughes et al. | 424/433 |

OTHER PUBLICATIONS

Tang et al. Antiviral Research 13:313–326, 1990.
Lavie et al, Ann N.Y. Acad Sci. 616:556–562, 1990.
Hudson et al, Planta Med 60:329–332, 1994.
Kraus et al, Biochemical Biophysical Res Comm 172(1):149–153 1990.
Hudson et al, Antiviral Research 15:101–112, 1991.
Kochel et al, Int. J. Cancer 48:682–688, 1991.
Green et al, Virology 110:176–184, 1981.
Paul, W. E., "Fundamental Immunology", Raven press, pp. 985–993, 1989.
Meruelo, D. et al (1988) Proc. Natl. Acad. Sci. USA 85:5230–5234.
Lavie, G. et al (1989) Proc. Natl. Acad. Sci. US–86:5963–5767.

*Primary Examiner*—Hazel F. Sidberry
*Assistant Examiner*—Julie Krsek-Staples
*Attorney, Agent, or Firm*—Browdy and Neimark

[57] ABSTRACT

A method for treating a papilloma virus infection comprising topically administering hypericin which is effective to inhibit the replication, growth and/or the infectivity of the virus. The papilloma viruses include those capable of causing benign warts or a malignancy such as human papilloma virus-1 (HPV-1), HPV-2, HPV-6, HPV-11, HPV-16 and HPV-18.

6 Claims, 10 Drawing Sheets

METHOD OF TREATING PAPILLOMA VIRUS INFECTION USING HYPERICIN

The present application is a continuation-in-part of U.S. Ser. No. 07/821,945, filed as PCT/US93/00364, Jan. 19, 1993, abandoned, which is entirely incorporated herein by reference.

BACKGROUND OF THE INVENTION

1. Field of the Invention

The invention, in the fields of virology, immunology and medicine, relates to a method for inactivating a pathogenic microorganism or virus and/or enhancing its immunogenicity by treating the microorganism or virus with a polycyclic aromatic hydrocarbon, preferably hypericin or an analog thereof. The invention also provides a method for producing a vaccine, comprising inactivating a microorganism or virus in a way which preserves and enhances its immunogenic properties using the method of the invention, vaccines produced by this method, and methods for vaccinating against a disease, comprising immunization with the vaccine of the present invention.

2. Description of the Background Art

Vaccination against bacterial or viral induced diseases is an old concept which dates back to Louis Pasteur. The first vital vaccine devised by Lister involved the inoculation of humans with cow pox virus (Vaccinia) to obtain immunity against the human pox virus (Variola). Since then, a wide variety of vaccines against numerous childhood diseases such as mumps, measles and German measles (Rubella), as well as against poliovirus and Hepatitis B virus have been developed and approved for use.

The requirements for a vaccine against a disease-causing virus have been defined. Effective vaccine preparations must exhibit several properties described below.

The virus preparation in the vaccine must be rendered non-infectious either by killing the virus or, in the case of live virus vaccines, attenuating the virus. Infectivity is completely abolished by subjecting the virus to processes of inactivation which essentially kill the virus. Often, however, complete inactivation of the virus results in reduced protective capacity. This phenomenon is perhaps best known in polio virus vaccines, wherein the live virus vaccine (the Sabin vaccine) has a superior protective index compared to the killed virus vaccine (the Salk vaccine). However, whereas there are no reports of disease caused by the Salk vaccine, the Sabin vaccine has caused disease in several hundred individuals.

The antigenic properties of the virus in the vaccine preparation must be preserved. Viral antigenic determinants must be available for recognition, processing and presentation by antigen-presenting cells of the immune system of the vaccinated individual. The immunity which is elicited against these antigenic determinants must be capable of reacting with an invading virus to inactivate it before it causes disease. A major goal in vaccine preparation is to enhance the immunogenicity of those antigenic determinants which are important for protective immunity but are often weak immunogens.

This process is most commonly achieved in two ways, often used in combination. First, adjuvants are incorporated into vaccines to enhance non-specifically the immune response against the viral components. Examples for such adjuvants are the pertussis in the Diphtheria-Pertussis-Tetanus (DPT) vaccine, or lipid fractions derived from mycobacteria.

Second, advantage is taken of the knowledge that immune reactions against antigens in particulate form are considerably stronger and more prolonged than responses to soluble antigens. The particulate form slows down the turnover of the antigens and the rate of their degradation. Since clearance from the body is prolonged, the immune system is exposed to more protracted stimulation by the antigen. Because of this consideration, many vaccines are formulated to achieve a particulate form of the antigen. The most common approaches in use involve precipitation of viral components on aluminum hydroxide (alum precipitation).

Modern molecular biology and recombinant DNA technology has also revolutionized the vaccine field. It has enabled the engineering of recombinant and genetically modified viruses from which deleterious disease-inducing genes and other undesirable regulatory genes have been deleted. By such methods, DNA encoding the most important antigens, in particular viral surface antigens, are cloned in bacterial and yeast systems and the antigens obtained therefrom in high yield for immunization. Some recent recombinant vaccine preparations encompass only such selected antigens (Sumner, J. W. et al., *Virology* 183:703–710 (1991); Gotch, F. M. et al., *AIDS* 5:317–320 (1991); Taylor, J. et al., *J. Virol.* 65:4263–4274 (1991). In other approaches, DNA encoding surface proteins from a pathogenic virus is packaged in a "chimeric" non-pathogenic virus (such as Vaccinia), and this new engineered virus serves as the immunizing preparation.

As mentioned above, inactivation of a pathogenic virus, such as a retrovirus, is often an essential step in the preparation of a vaccine. Numerous methods of inactivation are presently in use. These include fixation and cross-linking of the virus with formaldehyde or glutaraldehyde, heat inactivation, or inactivation with heavy metal salts such as cesium chloride and others. Nevertheless, there, is still a well-recognized need for improved means of virus inactivation for production of vaccines with greater efficacy, safety and other desirable qualities.

Hypericin is an aromatic polycyclic dione compound which has previously been found to possess photodynamic properties (Duran et al., *Photochem. Photobiol.* 43:677–689 (1986); Giese *Photochem. Photobiol. Rev.* 5:229–255 (1980)). In the presence of light (and possibly other sources of energy), this compound excites oxygen to its singlet state and is capable of generating superoxide radicals which can lead, among other things, to oxidation of tryptophan imidazole groups in proteins and oxidation of fatty acids in biological systems.

The present inventors and their colleagues have investigated the use of hypericin and its quinone-containing analogs in the inactivation of retroviruses. See, for example, U.S. Pat. No. 5,047,435; Degar et al., In: *HIV Disease: Pathogenesis and Therapy*, University of Miami, 1991, abstract No. 1–16; Lavie et al., *Fifth Int'l Conf. on AIDS*, Montreal, 1989, abstract C.501; Lavie et al. *Proc. Natl. Acad. Sci. USA* 86:5963–5967 (1989); Lavie et al. *Ann. New York Acad. Sci. USA* 616:556–562 (1990); Lavie, G. et al., In: *HIV Disease: Pathogenesis and Therapy*, University of Miami, 1991, abstract 1–27; Meruelo, D. et al., *Proc. Natl. Acad. Sci. USA* 85:5230–5234 (1988); Meruelo, D. et al. In: *HIV Disease: Pathogenesis and Therapy*, University of Miami, 1991, abstract 1–291; Valentine et al., *Fifth Int'l Conf. on AIDS*, Montreal, 1989, abstract M. C. P. 18; Weiner et al., *Fifth Int'l Conf. on AIDS*, Montreal, 1989, abstract C-608.

SUMMARY OF THE INVENTION

In their studies of compounds which inactivate viruses, in particular retroviruses, the present inventors discovered that the process of inactivation of a virus with hypericin and related compounds also can preserve and enhance the immunogenicity of the virus. Thus, the present inventors conceived of the use of such compounds in treating a protein or peptide, as well as a microorganism or virus containing the protein or peptide, in the production of a vaccine useful for immunization against virtually any type of pathogenic microorganism or virus.

In one embodiment, the present invention provides a method for producing a protein- or peptide-containing agent with enhanced immunogenicity, comprising: (a) treating a protein- or peptide-containing agent with hypericin, protohypericin, or a hypericin or protohypericin analog or derivative capable of enhancing the immunogenicity for a time sufficient to enhance the immunogenicity; and (b) terminating the treatment of step (a), preferably by dilution. In the above method hypericin, protohypericin, or an analog or derivative thereof, is preferably selected from the group consisting of hypericin, pseudohypericin, desmethyl hypericin, hypericin diacetate, hypericin hexaacetate, hypericin methyl ester, hypericin propyl ester, and salts thereof, including ion pairs of hypericin with sodium, potassium, lithium, lysine, glutamine, ethylenediamine, TRIS, N-methyl glucamine, diethanolamine, triethanolamine, and others.

The protein or peptide-containing agent for which the above method is useful includes a virus, a bacterium, or a parasite. In another embodiment, the agent can be a portion of a virus, bacterium or parasite, including a simple protein or peptide. Preferred viruses are retroviruses, including HIV-1, HIV-2, HTLV-1, HTLV-II, feline leukemia virus, feline immunodeficiency virus, avian myeloblastosis virus or avian leukosis virus. Alternatively, the virus may be selected from the group consisting of papilloma virus, influenza virus, parainfluenza virus, Herpes Simplex Virus type 1, Herpes Simplex Virus type 2, cytomegalovirus, Epstein-Barr virus, Dengue virus and rhinovirus.

In another embodiment, the present invention is directed to a method for eliminating the infectivity of a pathogenic microorganism or virus while retaining the immunogenicity in the process of producing a vaccine, comprising:
(a) treating the microorganism or virus with hypericin, protohypericin, or a hypericin or protohypericin analog or derivative capable of inactivating the microorganism or virus for a period of time sufficient to eliminate the infectivity of the microorganism or virus while retaining its immunogenicity; and (b) terminating the treatment of step (a), preferably by dilution. Preferably, hypericin or a hypericin analog or derivative is selected from the group consisting of hypericin, pseudohypericin, desmethyl hypericin, hypericin diacetate, hypericin hexaacetate, hypericin methyl ester, hypericin propyl ester, isopropyl desmethyl hypericin, butyl ester of hypericic acid, and salts thereof, including ion pairs of hypericin with sodium, potassium, lithium, lysine, glutamine, ethylenediamine, TRIS, N-methyl glucamine, diethanolamine, triethanolamine, and others.

A preferred use of the above method is for treating a virus. Preferred viruses are retroviruses, including HIV-1, HIV-2, HTLV-1, HTLV-II, feline leukemia virus, feline immunodeficiency virus, avian myeloblastosis virus or avian leukosis virus. Alternatively, the virus may be selected from the group consisting of papilloma virus, influenza virus, parainfluenza virus, Herpes Simplex Virus type 1, Herpes Simplex Virus type 2, cytomegalovirus, Epstein-Barr virus, Dengue virus and rhinovirus.

In a method for inducing immunity in a subject to a protein- or peptide-containing agent by immunizing the subject with a vaccine which includes an antigen of the protein- or peptide containing-agent against which immunity is desired, the present invention provides an improvement wherein the vaccine is produced by incubating the agent with an effective concentration of hypericin or a hypericin analog or derivative capable of enhancing the immunogenicity of the agent for a time sufficient to enhance the immunogenicity of the agent, wherein, when the agent is an infectious agent, the infectivity of the agent is eliminated.

In another method, treatment of papilloma virus infection in an animal subject is provided, comprising administering a pharmaceutically acceptable amount of a hypericin, analog or derivative thereof, which is effective to inhibit the replication, growth and/or infectivity of a papilloma virus. Preferably the papilloma virus is selected from a "low risk" group of papilloma viruses associated with benign warts or lesions; and a "higher risk" group of papilloma viruses associated with lesions or warts which can progress to a malignant state.

Another method is provided for inactivating a virus, comprising contacting the virus with an inhibitory effective amount of hypericin, hypericin analog, or derivative or salt thereof. Preferably, the virus is selected from a retrovirus or a papilloma virus. The papilloma virus may be capable of causing benign warts or a malignancy.

In the above methods, hypericin or a hypericin analog or derivative is preferably selected from the group consisting of hypericin, pseudohypericin, desmethyl hypericin, hypericin diacetate, hypericin hexaacetate, hypericin methyl ester, hypericin propyl ester, isopropyl desmethyl hypericin, butyl ester of hypericic acid, and salts thereof, including ion pairs of hypericin with sodium, potassium, lithium, lysine, glutamine, ethylenediamine, TRIS, N-methyl glucamine, diethanolamine, triethanolamine, and others.

In this method, the agent is preferably a virus, a bacterium or a parasite. Preferably, the virus is a retrovirus, including HIV-1, HIV-2, HTLV-1, HTLV-II, feline leukemia virus, feline immunodeficiency virus, avian myeloblastosis virus and avian leukosis virus. Alternatively, the virus may be selected from the group consisting of papilloma virus, influenza virus, parainfluenza virus, Herpes Simplex Virus type 1, Herpes Simplex Virus type 2, cytomegalovirus, Epstein-Barr virus, Dengue virus and rhinovirus.

In another embodiment, the above method further comprises inactivating the agent by treating with formaldehyde or glutaraldehyde, by heat treatment, by treatment with acid pH, or with heavy metal salts, such as cesium chloride.

The present invention further provides a vaccine useful for prevention of a disease caused by a microorganism or virus consisting essentially of (a) a protein- or peptide-containing agent previously incubated with hypericin or protohypericin, or an analog or derivative thereof; and (b) a pharmaceutically acceptable carrier or excipient.

In a preferred vaccine, the protein or peptide-containing agent is a pathogenic microorganism or virus, preferably a retrovirus or a lentivirus, including HIV-1, HIV-2, HTLV-1, HTLV-II, avian myeloblastosis virus and leukosis virus, feline leukemia virus and feline immunodeficiency virus. In a most preferred vaccine, the retrovirus is HIV-1 or HIV-2 and the disease treated is AIDS.

In another embodiment, the above vaccine is for a virus selected from the group consisting of papilloma virus, influenza virus, parainfluenza virus, Herpes Simplex Virus type 1, Herpes Simplex Virus type 2, cytomegalovirus, Epstein-Barr virus, Dengue virus and rhinovirus.

Also provided is a pharmaceutical composition useful for preventing or treating a disease caused by a microorganism comprising a vaccine as above and an additional therapeutic agent useful in the treatment of the disease.

In another embodiment, the vaccine includes any of the above-mentioned viruses inactivated with hypericin in combination with other modes of inactivation, such as heat, acid pH, fixatives such as formaldehyde or glutaraldehyde and/or heavy metal salts such as cesium chloride. The inactivated virus vaccine can be formulated in combination with other acceptable adjuvants such as precipitation with aluminum hydroxide.

DETAILED DESCRIPTION OF THE PREFERRED EMBODIMENTS

Figure 1:
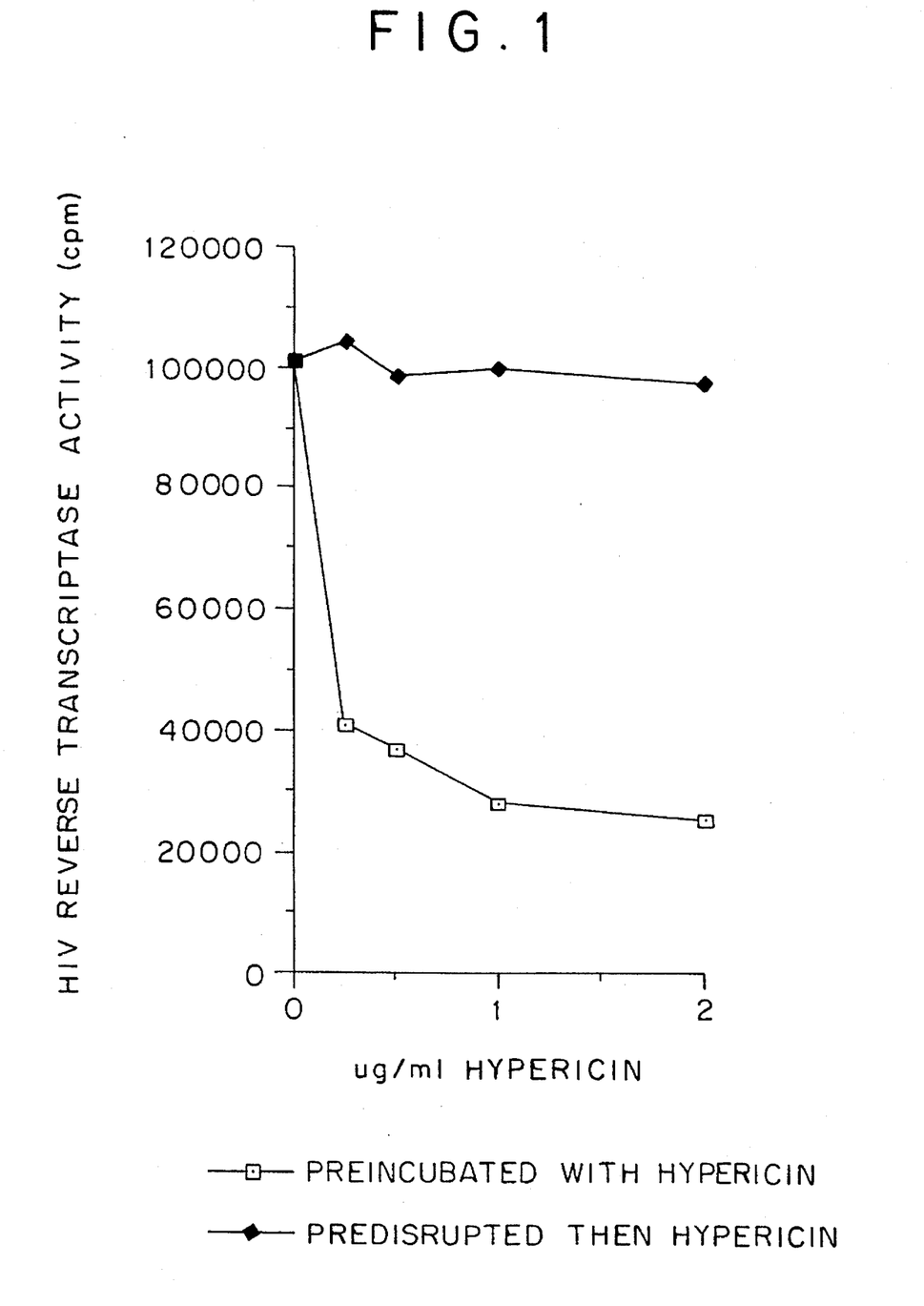
FIG. 1 is a graph showing that treatment with hypericin prevents detergent-mediated (0.5–1% Triton X-100) release of reverse transcriptase activity from viral particles.
Figure 2:
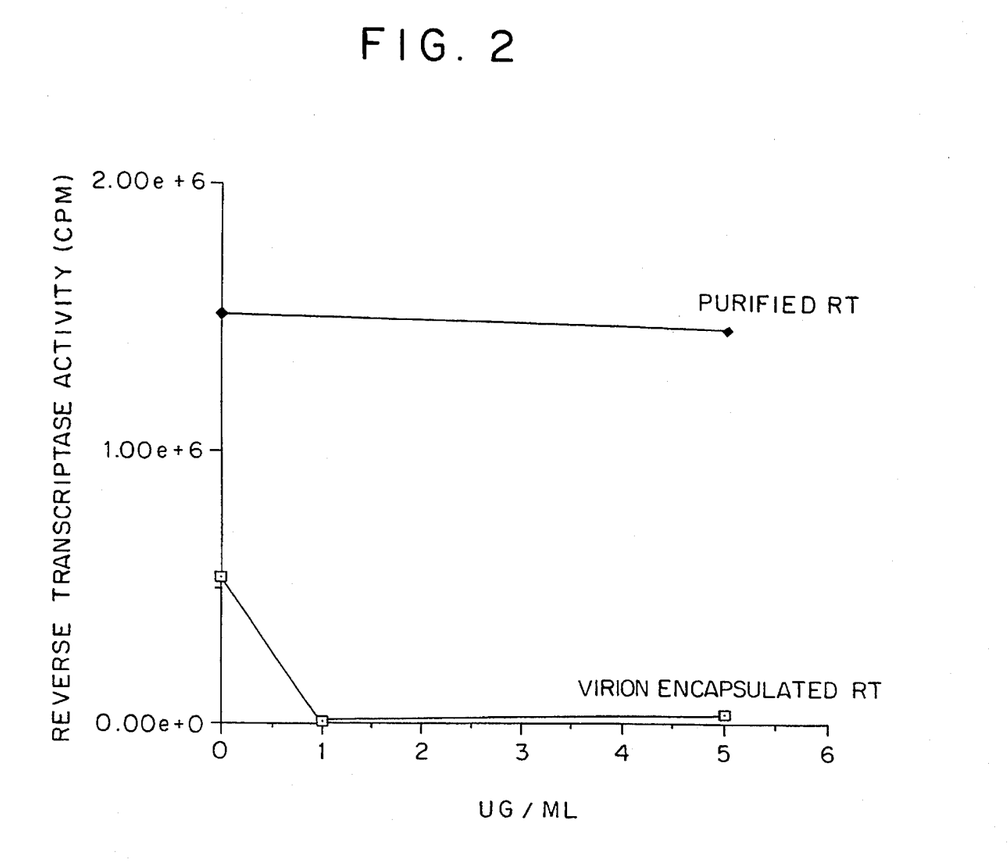
FIG. 2 is a graph showing that hypericin does not directly affect enzymatic activity of purified reverse transcriptase enzyme under the assay conditions used.
Figure 3:
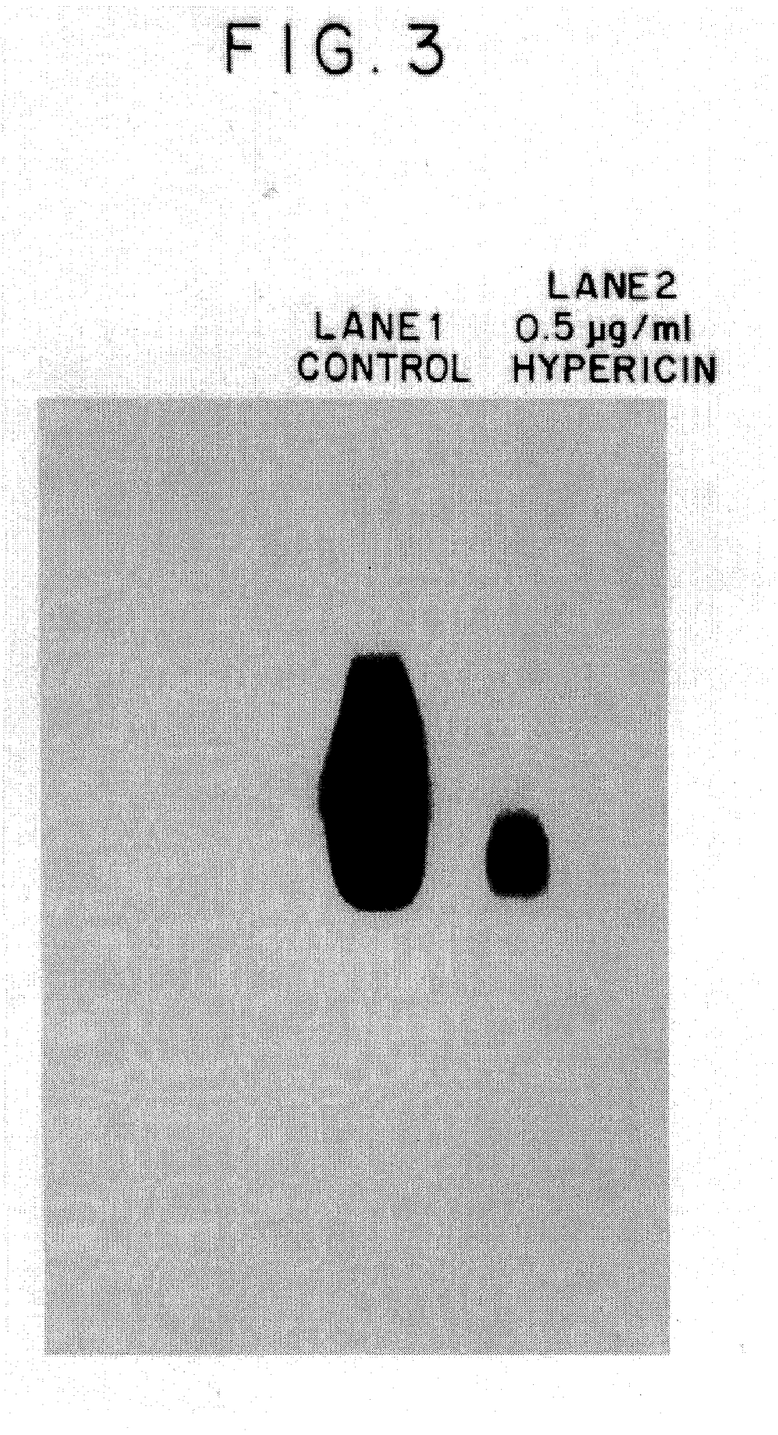
FIG. 3 is an electrophoresis gel pattern showing dramatic inhibition of the ability of guanidinium hydrochloride to extract RNA from virions treated with hypericin prior to guanidinium hydrochloride disruption.

The present invention relates to the discovery that, following treatment of retroviral particles with hypericin, protohypericin, analogs, derivatives or salts thereof, the virion becomes more resistant to disruption with non-ionic detergents, such as 1% aqueous solutions of Triton X-100, and ionic detergents such as 0.1% SDS (sodium dodecyl sulfate). (See FIGS. 1–3).

The present invention also relates to the inactivation of a papilloma virus or retrovirus by contact or treatment of a subject so infected therewith with hypericin, protohypericin, analogs, derivates or salts thereof.

The present inventors have further discovered that hypericin-treated retroviral particles become more resistant to dissociation by harsh denaturing reagents such as guanidinium hydrochloride (GuHCl). These denaturing agents effectively disrupt hydrogen bonding, thereby unfolding tertiary and quaternary structures of proteins and causing dissociation of bonded proteins and the collapse of biological structures.

When GuHCl was used to extract viral RNA from hypericin-treated retroviral particles of a murine retrovirus, Radiation leukemia virus (RadLV), yields of extractable RNA were markedly reduced, indicating that the RNA remained entrapped within the rigidified virus particle. These findings suggested to the present inventors that hypericin induced covalent cross-linking of viral components to form a non-dissociable capsid structure.

Treatment of a retrovirus, for example the murine Friend leukemia virus (FLV) with hypericin, protohypericin, analogs, derivatives or salts thereof, also resulted in preservation and enhancement of the antigenic properties of the virus and in the ability of the hypericin-treated virus preparation to serve as an immunogen and elicit immune responses in a mammalian host (in the case of FLV, in mice).

Treatment of a papilloma virus or papilloma virus infection with hypericin, protohypericin, analogs, derivatives or salts thereof is also found to be effective in inhibiting the growth, replication, infectivity and/or clinical symptoms such as wart formation.

Figure 4:
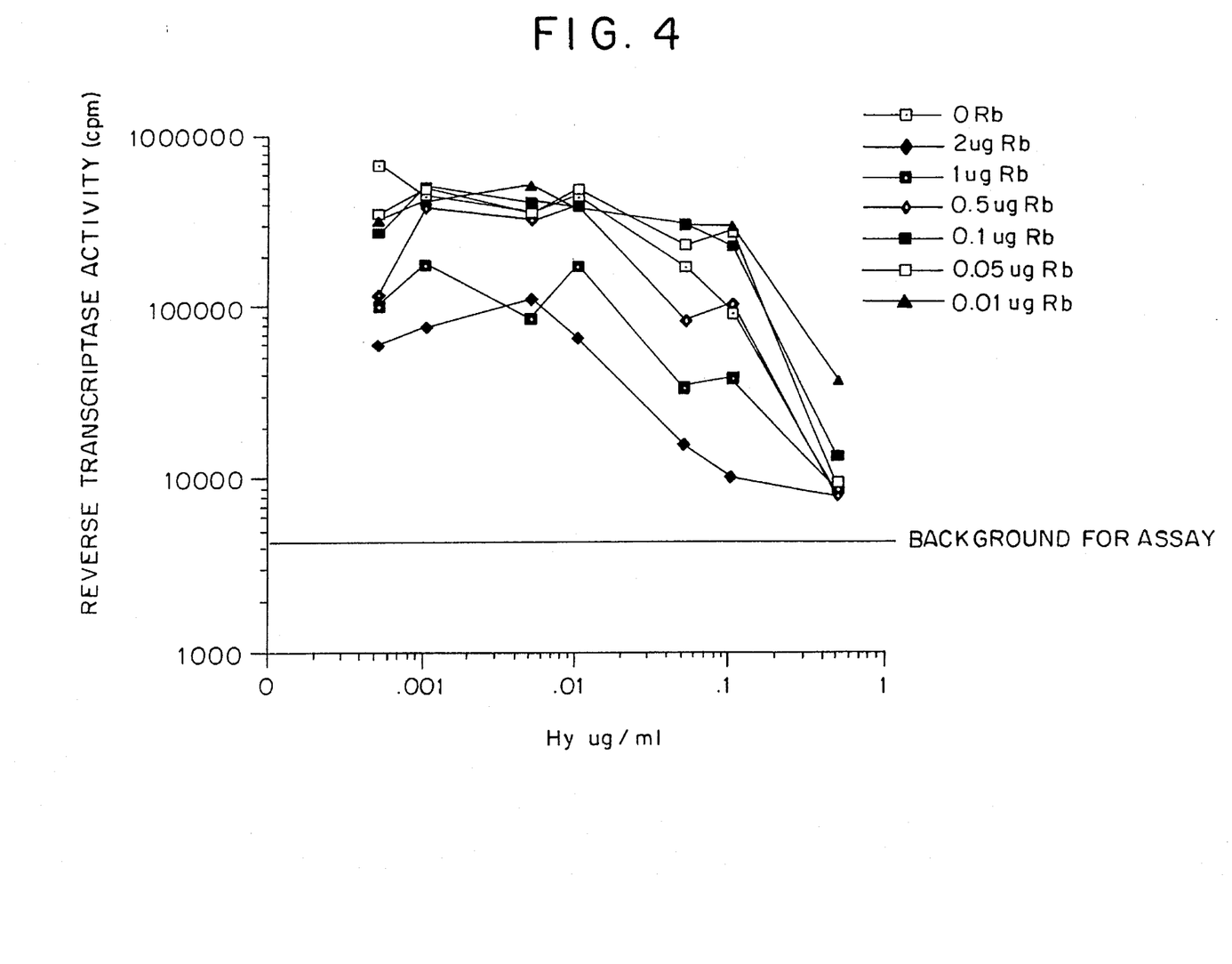
FIG. 4 is a graph showing that Rose Bengal (Rb) (1–2 μg/ml) enhances the ability of hypericin (0.001–1 μg/ml) to inactivate murine RadLV particles which were produced from the AQR cell line, a murine thymoma. Assays for virus particle-derived reverse transcriptase were performed according to Stephenson, J. R. et al., Virology 48:749–756 (1972)).
Figure 8:
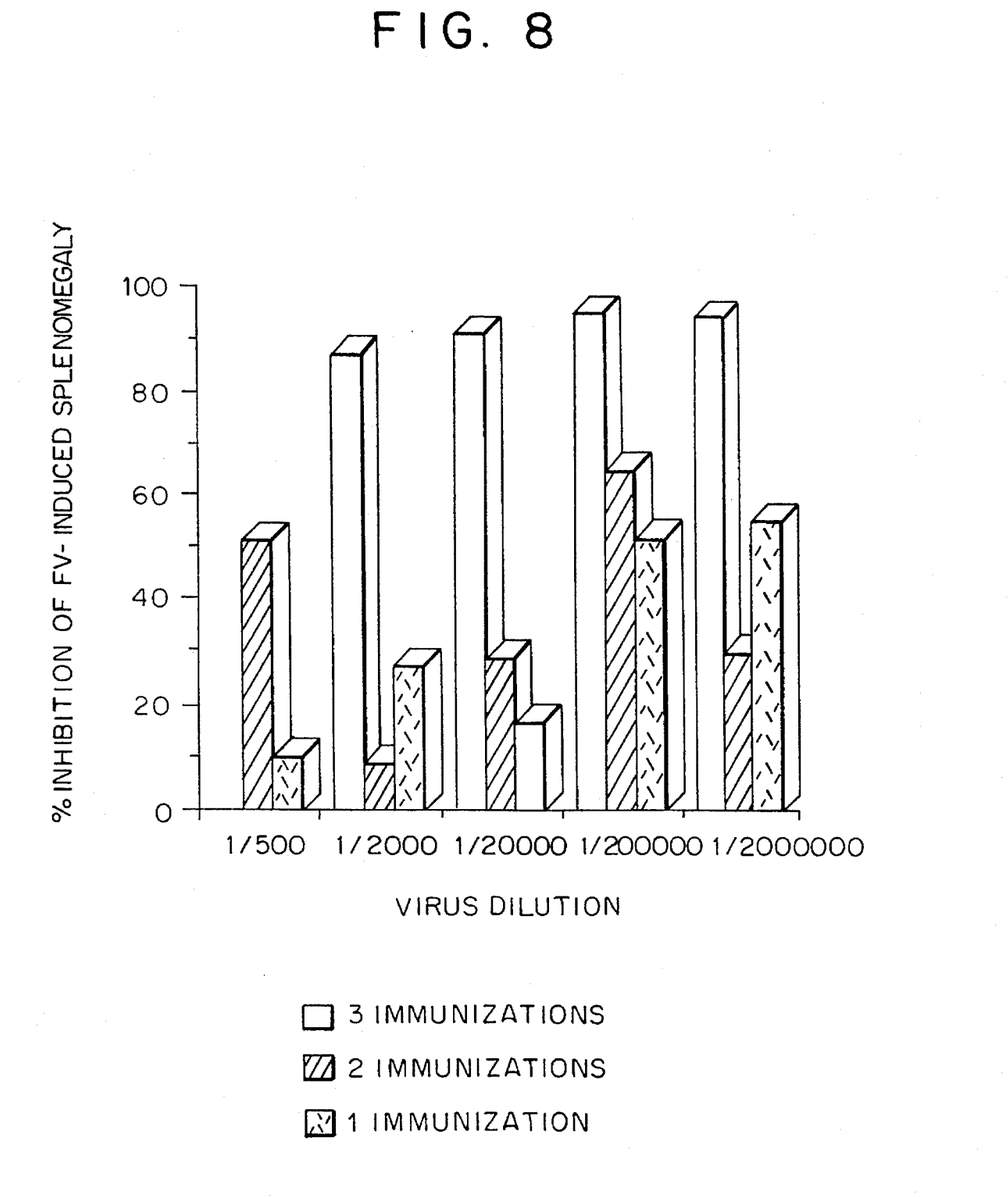
FIG. 8 is a graph showing that three immunizations with a hypericin-treated Friend leukemia virus preparation successfully immunized mice against a virus challenge with a very high titer virus preparation. The challenge dose, when diluted $2\times10^6$-fold, still induced marked splenomegaly in infected mice.

Hypericin is a photodynamic agent which, in the presence of light, produces excited oxygen species such as singlet oxygen and superoxide radicals. These excited oxygen species play a role in the antiviral and antiretroviral activity of hypericin and hypericin analogs. While this property of producing excited oxygen species may account for inactivation of the virus or retrovirus particle, it is not sufficient to explain the enhanced immunogenicity of the inactivated virus. Support for this notion comes from experimental findings by the present inventors using another photodynamic agent, Rose Bengal. Rose Bengal also produces excited oxygen species, is also capable of inactivating retroviral particles and interacts synergistically with hypericin in inactivating the virus. Thus, with concentrations of hypericin ranging from 0.001 to 1 μg/ml (and up to 100 μg/ml) Rose Bengal at concentrations of 1–2 μg/ml (and up to between 0.01 and 50 μg/ml) enhanced the ability of hypericin to inactivate retroviral particles (FIGS. 4 and 8). However, Rose Bengal does not cause marked enhancement of immunogenicity and may even diminish hypericin-induced enhancement of immunogenicity (see Example IV, below).

According to the present invention, hypericin treatment of a retrovirus significantly enhances the immunogenicity of the treated viral preparation. The material being treated to enhance immunogenicity, whether free or complexed proteins or peptides, or native or treated microorganisms, is incubated with an effective concentration of hypericin for a time sufficient to result in enhanced immunogenicity.

For enhancing immunogenicity according to the present invention, a concentration between about 0.001 and about 500 µg/ml is preferred. More preferably, a concentration between about 0.1 and 50 µg/ml is used. The time period of incubation is between 0.5 and 6 hours, and for some viruses, 24 or even 48 hours. The preferred time is that which will permit elimination of infectivity while retaining or enhancing the immunogenicity. For The method of this invention has been proven effective against an aggressive, acute oncogenic retrovirus, FLV, which induces rapid proliferation of hemopoietic precursor cells, resulting in fulminant erythroleukemia and rapid death. When administered to BALB/c mice at the doses described herein, FLV virus induces splenomegaly observed as about a 4–6 fold increase in spleen size in 10 days and death of 100% of the subjects within 22–45 days.

A single intraperitoneal administration of a FLV preparation exposed to 5 µg/ml hypericin for only 1 hour is sufficient to elicit protection from subsequent infection by a challenge with live, fully infectious FLV (see Example III). Successful inactivation of the virus by hypericin was evidenced by the absence or presence of minimal splenomegaly in mice receiving the immunizing dose of FLV.

According to the present invention, a live virus challenge at an appropriate time after initial immunization, when immunity is present, results in significant protection against the virus-induced disease. A single immunizing dose may produce protection in a range of approximately 80–90% (compared to unimmunized subjects). This is measured in a murine model by FLV-induced splenomegaly 15 days after challenge.

As discussed above, a particulate form of virus vaccine is considered optimal for immunization, particularly for vaccination aimed at eliciting powerful and long lasting immune responses. Treatment of a virus with hypericin provides such a particulate preparation. When hypericin-treated RadLV radiolabeled with $^{35}$S-methionine is subjected to 0.1% SDS denaturation and analyzed on SDS-polyacrylamide gel electrophoresis, aggregates of virus components can be observed to accumulate at the top of the gel and not to enter the matrix. Furthermore, when the virus is purified on a sucrose gradient, hypericin comigrates with the virus particles.

The high degree of protection obtained with a single dose immunization with hypericin-treated virus may reduce the need to incorporate adjuvants for enhancement of the immune response. The use of such adjuvants in vaccine preparations has recently become controversial following identification of severe side effects (albeit at low frequency). For example, arthritis has been observed in children immunized with the DPT vaccine, an effect attributed by some to the Pertussis adjuvant in the Diphtheria-Tetanus vaccine preparation.

The present invention is applicable to the development of a variety of vaccines, wherein hypericin or a hypericin analog is used to inactivate and render more immunogenic other pathogens, viruses, antigens and the like, in the presence of light (preferably fluorescent neon light), or by additional heat treatment or other forms of inactivation.

According to the present invention, other molecules may be incorporated which can secure even more complete inactivation of the virus particles in a preparation without jeopardizing the immunogenicity of the preparation. This is desirable when inactivating a virus preparation having a very high titer (e.g., more than $10^4$ tissue culture infectious doses, TCID$_{50}$).

Preferred retroviruses of the present invention include both human and other animal retroviruses. Preferred human retroviruses include Human Immunodeficiency Virus-1 (HIV-1), Human Immunodeficiency Virus-2 (HIV-2), Human T-Cell Lymphotropic Virus-1 (HTLV-1), and Human T-Cell Lymphotropic Virus-2 (HTLV-2). Also intended within the scope of the present invention are additional retroviruses of other animal species, most particularly agriculturally important animals such as cows and chickens, and pets such as dogs and cats. A non-limiting list of additional retroviruses included within the scope of the present invention is provided in Table I, below. Retroviruses are described in detail in Weiss, R. et al. (eds), RNA Tumor Viruses. "Molecular Biology of Tumor Viruses," Cold Spring Harbor Laboratory, Cold Spring Harbor, N.Y., 1984, which is hereby incorporated by reference.

TABLE I

Animal Retroviruses

Avian Erthyroblastosis Virus
Avian Leukosis Virus (or Lymphoid Leukosis Virus)
Avian Myeloblastosis Virus
Baboon Endogenous Virus
Bovine Leukemia Virus
Bovine Syncytial Virus
Caprine Encephalitis-Arthritis Virus (or Goat Leukoencephalitis Virus)
Avian Myelocytomatosis Virus
Corn Snake Retrovirus Chicken Syncytial Virus
Duck Infectious Anemia Virus
Deer Kidney Virus
Equine Dermal Fibrosarcoma Virus
Equine Infectious Anemia Virus
Esh Sarcoma Virus
Feline Leukemia Virus
Feline Sarcoma Virus
Feline Syncytium-forming Virus
Fujinami Sarcoma Virus
Gibbon Ape Leukemia Virus (or Simian Lymphoma Virus or Simian Myelogenous Leukemia Virus)
Golden Pheasant Virus
Lymphoproliferative Disease Virus
Myeloblastosis-associated Virus
Myelocytomatosis Virus
Mink Cell Focus-Inducing Virus
Myelocytomatosis Virus 13
Mink Leukemia Virus
Murine Leukemia Virus
Mouse Mammary Tumor Virus
Mason-Pfizer Monkey Virus
Murine Sarcoma Virus
Myeloid Leukemia Virus
Myelocytomatosis Virus
Progressive Pneumonia Virus
Rat Leukemia Virus
Rat Sarcoma Virus
Rous-Associated Virus 0
Rous-Associated Virus 60
Rous-Associated Virus 61
Reticuloendotheliosis-Associated Virus
Reticuloendotheliosis Virus
Reticuloendotheliosis Virus-Transforming
Ring-Necked Pheasant Virus
Rous Sarcoma Virus
Simian Immunodeficiency Virus
Simian Foamy Virus
Spleen Focus-Forming Virus
Squirrel Monkey Retrovirus
Spleen Necrosis Virus
Sheep Pulmonary Adenomatosis/Carcinoma Virus
Simian Sarcoma-Associated Virus (or Wooly Monkey Leukemia Virus)
Simian Sarcoma Virus (or Wooly Monkey Virus).
Visna Virus DNA viruses for which the methods and vaccines of the present invention are useful include the Herpesviridae, such as, for example, HSV-1, HSV-2, cytomegalovirus and Epstein-Barr virus in humans, Marek's disease virus in chickens, and pseudorabies virus in other animals. Other viruses include Dengue virus, influenza virus, and rhinovirus.

Papilloma viruses are also inactivated by treatment with hypericin or hypericin analogs. A vaccine preparation of a papilloma virus can therefore also be produced by inactivation with hypericin or hypericin analogs as disclosed herein for other viruses. Alternatively, hypericin or hypericin analogs can be administered topically or systemically to treat papilloma infections in animals.

Accordingly, a method for inactivating a virus is provided, comprising contacting the virus with an inactivating effective concentration of a hypericin, protohypericin, or an analog, derivative or salt thereof. As presented herein, the virus may be a papilloma virus or a retrovirus.

The contacting may be in solution, topically or systemically, as described herein. The papilloma virus may be benign wart or lesion inducing or malignancy inducing. Examples of benign wart or lesion inducing papilloma viruses include, but are not limited to, human papilloma virus (HPV) 1, 2, 6 and 11. HPVs known to be capable of inducing malignancy are HPV-16 and HPV-18. Both types of papilloma virus are found in pathologies such as genital warts and exophytic papillomas other than nasal exophytic papillomas. Benign warts or tumors may be caused by papilloma virus infection, such as in juvenile papillomas (as in the larynx), nasal exophytic papillomas and dermal warts. Malignancy induced papilloma viruses may be associated with genital warts, inverted papillomas, genital cancer or other warts.

The preferred animal subject of the present invention is a mammal, although it is expected to be operable in birds, fish, reptiles and other animals having the required immune systems. By the term "mammal" is meant an individual belonging to the class Mammalia. The invention is particularly useful in the treatment of human subjects.

By the term "treating" is intended the administering to subjects a hypericin or pseudohypericin compound, derivative, analog or salt, an inactivated protein, a peptide or a microorganism according to the method of the present invention, or a vaccine or pharmaceutical composition of the present invention, for purposes which may include prevention, amelioration, or cure of a disease caused by the microorganism or virus.

A pharmaceutical composition of the present invention may be comprised of the vaccine of the present invention, or hypericin or a hypericin or derivative, analog, alone or in combination with another therapeutic agent or agents or modalities. Examples of such therapeutic agents for treatment of viral diseases include hypericin or any other antiviral or antiretroviral agent, such as an anti-AIDS drugs which are well-known in the art. Other agents are those directed against another pathogenic microorganism, such as an antibacterial, antifungal or antiparasitic agent, or an agent used to treat the symptoms of the disease produced by that microorganism. The combination of the vaccine of the present invention, or hypericin or analog, and the optional additional therapeutic agent or agents is preferably provided to the subject concurrently. However, the time between the administration of the vaccine, hypericin, analog or derivative, and the other therapeutic agent may be varied to permit an overlap of biological activity. The pharmaceutical composition or combinations thereof with another therapeutic agent or agents can be administered topically, systemically or to one or more different sites in the body in order to achieve a heightened state of regional immunity, for example to protect against gastrointestinal, vaginal, oral or systemic routes of infection.

In addition to the vaccine preparation or hypericin analog or derivative, the pharmaceutical composition of the present invention may contain a suitable pharmaceutically acceptable carrier comprising an excipient and auxiliary which facilitates processing of the active compound into preparations which can be used pharmaceutically. Preferably, the compositions contain from about 0.01 to 99 percent, more preferably from about 20 to 75 percent of active compound(s), together with the excipient.

The vaccine or pharmaceutical composition of the present invention may be administered by any means that achieves its intended purpose. Amounts and regimens for the administration of a vaccine or pharmaceutical composition can be determined readily by those with ordinary skill in the clinical art of treating infectious diseases.

For example, administration may be by parenteral, subcutaneous, intravenous, intramuscular, intradermal, intraperitoneal, genital, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the vaccine or hypericin or analog is contained in an amount effective to achieve its intended purpose. While individual needs vary, determination of optimal ranges of effective amounts of each component is within the skill of the art. Typical dosages comprise 0.00001 to 100 mg/kg/body wt. The preferred dosages comprise 0.0001 to 10 mg/kg/body wt. The most preferred dosages comprise 0.0001 to 1 mg/kg/body wt of the purified inactivated component, not including diluents, adjuvants and excipients.

Inactivation of the viral preparations to form the vaccine can be performed by solubilizing the virus in salt solutions containing human serum albumin or lipoproteins (HDL or LDL) or lipids such as phosphatidyl choline, phosphatidyl serine, or neutral lipids, and performed in the presence of neon light at 4° C. or, alternatively, at room temperature or heated to higher temperatures.

Virus may be inactivated with hypericin or a hypericin analog or derivative in combination with other modes of inactivation, such as heat inactivation, inactivation with a fixative such as formaldehyde or glutaraldehyde and/or heavy metal salts such as cesium chloride. In a preferred embodiment, the agent or virus is treated with formaldehyde or glutaraldehyde at a concentration of about 0.1 to about 3.0% for a period of about 10–30 minutes. In inactivation using heat treatment, the temperature and time used is a function of the type of agent; for example, conditions for heat-inactivation of different viruses are well-known in the art. In one embodiment, treatment at about 63° C. for about 30–60 minutes is used. In another embodiment, the virus or agent is treated at about 100° C. for about 1–30 minutes. The virus or agent may also be inactivated by treatment at acid pH, preferably at about pH 3.5 for a period of about 60 minutes.

The inactivated virus vaccine can be formulated in combination with other acceptable adjuvants such as precipitation with aluminum hydroxide, or vitamins A or E.

The pharmaceutical preparations of the present invention are manufactured in a manner which is itself known, for example, by means of conventional mixing, dissolving, or lyophilizing processes. Thus, pharmaceutical preparations for oral use can be obtained by combining the active compound with liquid excipients which form a suspension or with solid excipients, optionally grinding the resulting mixture and processing the mixture of granules, after adding suitable auxiliaries, if desired or necessary, to obtain tablets or dragee cores. Pharmaceutical preparations may also be prepared by precipitating the inactivated virus over aluminum hydroxide in a process known as "alum precipitation."

Suitable excipients are, in particular, proteins such as albumin (e.g., human serum albumin, lipids, saccharides, or aluminum hydroxide.

Suitable formulations for parenteral administration include aqueous solutions of the vaccine or hypericin or analog in water-soluble form. In addition, physiological solutions and solutions which contain human serum albumin or the serum albumin of the appropriate animal species for which protection or treatment by the vaccine or hypericin or analog is sought, phospholipids such as phosphatidyl choline, phosphatidyl serine and phosphatidyl ethanolamine. Another preferred formulation is in the form of a capsule, preferably an acid-resistant protective capsule designed to disintegrate in the jejunum at neutral or basic pH. Also contemplated are suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension include, for example, sodium carboxymethyl cellulose, sorbitol, dextran or propylene glycol. Optionally, the suspension may also contain stabilizers.

A pharmaceutical formulation for systemic administration according to the invention may be formulated for enteral, parenteral or topical administration. Indeed, all three types of formulation may be used simultaneously to achieve systemic administration of the active ingredient.

Suitable injectable solutions include intravenous, intradermal, subcutaneous and intramuscular injectable solutions. The vaccine or hypericin or analog may also be administered in the form of an infusion solution or as a nasal inhalation or spray. Suitable formulations for topical administration include creams, gels, jellies, mucilages, pastes and ointments.

The pharmaceutical formulation may include the inactivated virus preparation in combination with an acceptable adjuvant. For example the virus preparation may be precipitated with aluminum hydroxide. The adjuvant may be the Syntex vehicle mixture/adjuvant (Allison, A. C. et al., *J. Immunol. Meth.* 95:157–168 (1986)), a liposome carrier (see below), vitamin A or E carrier, or any other carrier of the vaccine preparation suitable for administration by any of the described routes.

Figure 5:
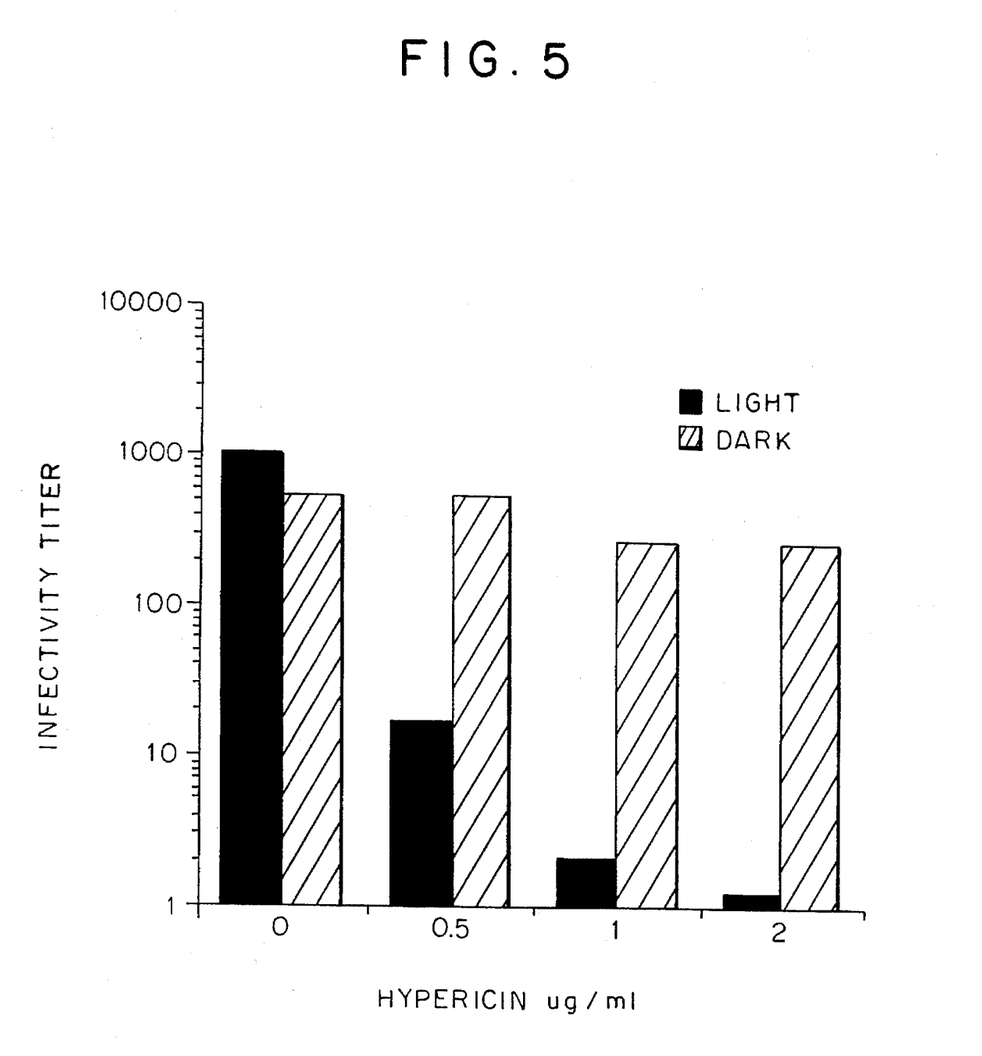
FIG. 5 is a graph showing the effect of ambient light treatment on hypericin's ability to reduce the infectivity titer of HIV for H9 target cells, measured in a limiting dilution assay.
Figure 6:
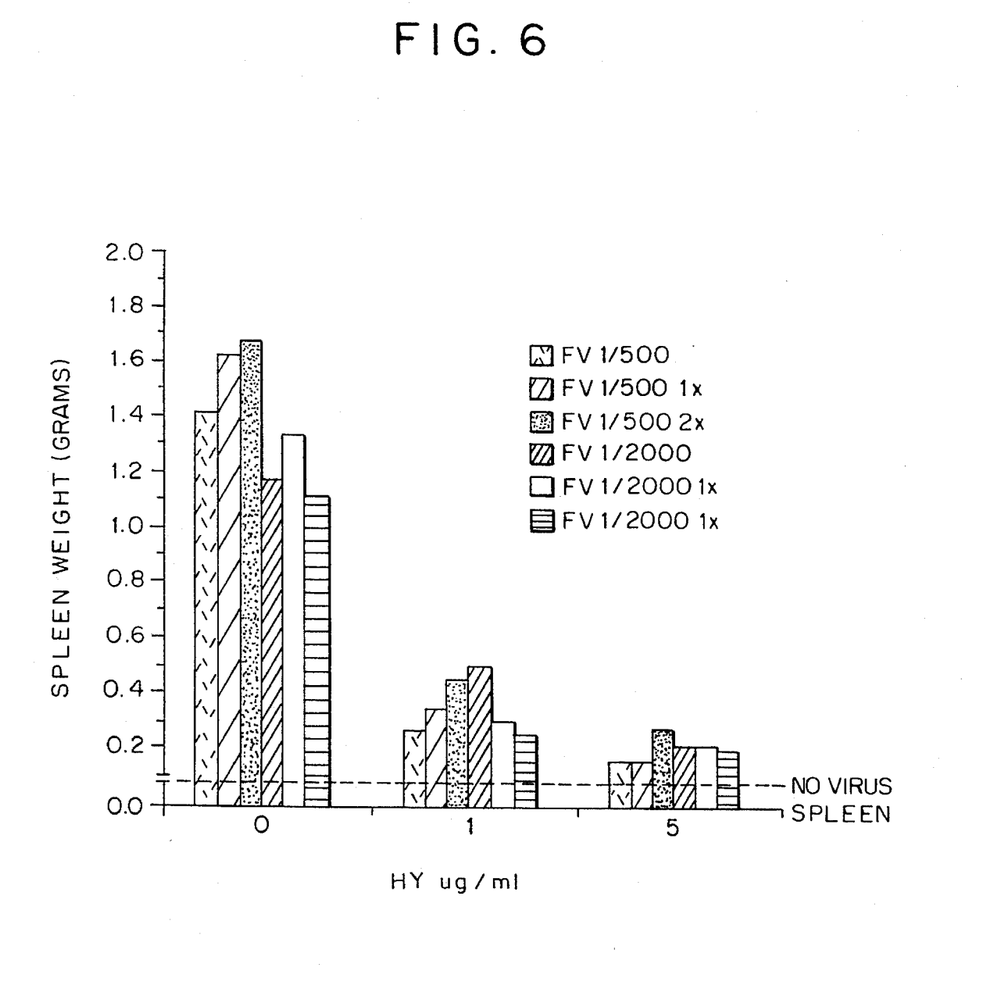
FIG. 6 is a graph showing the inactivation of Friend leukemia virus (FLV) extracorporeal treatment with hypericin. Virus infectivity is measured as splenomegaly. Uninfected mice generally have spleen weights in the range of 0.08 to 0.2 grams.
Figure 7:
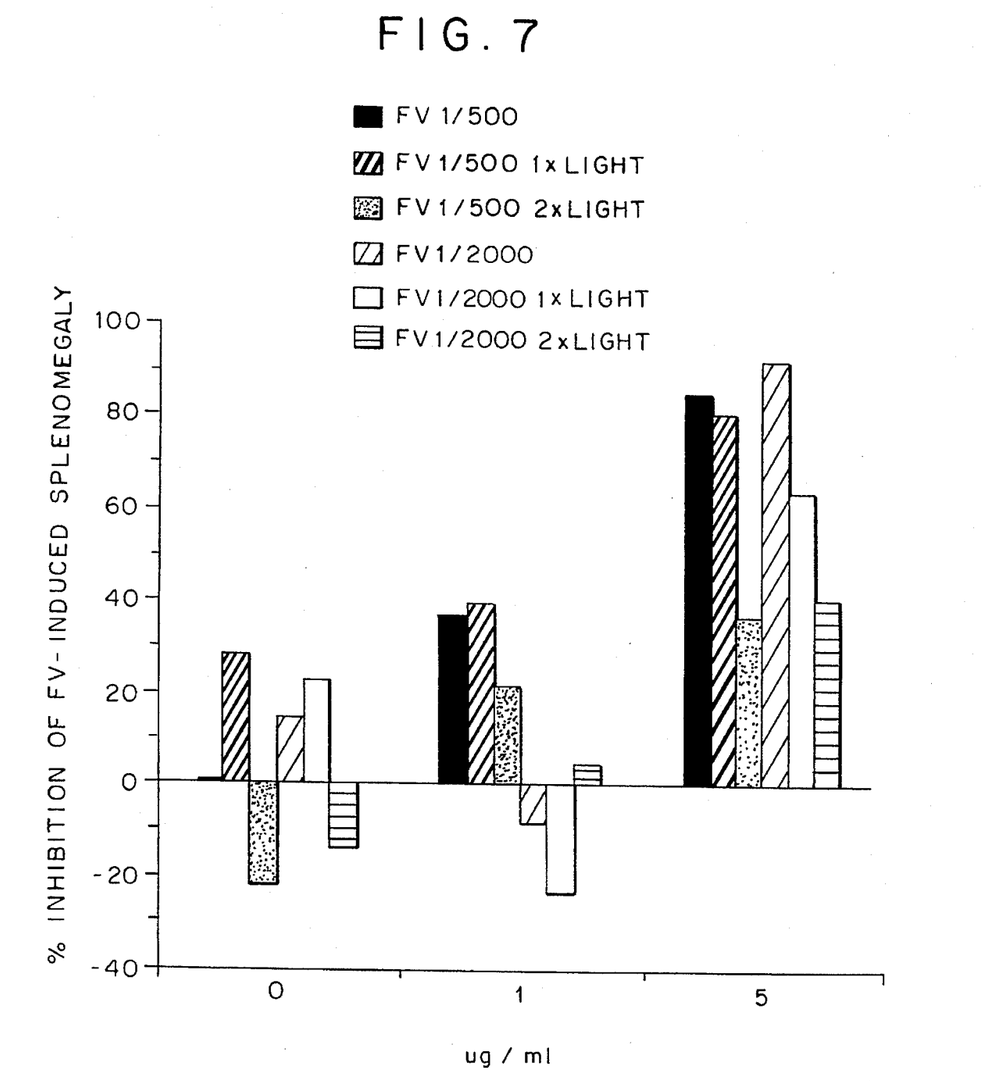
FIG. 7 is a graph showing that hypericin-treated Friend leukemia virus successfully immunizes mice against challenge with live virus. A single intraperitoneal administration of Friend virus exposed to hypericin at 5 μg/ml for only one hour was sufficient to elicit protective immunity which reduced splenomegaly by as much as 80–90%.

Other pharmaceutically acceptable carriers for the compounds according to the present invention are cyclodextrans. Also intended liposomes, pharmaceutical compositions in which the active ingredient is contained either dispersed or variously present in corpuscles consisting of aqueous concentric layers adherent to lipidic layers (see, for example, Gregoriades, G. et al., *Immunological Adjuvants and Vaccines,* Plenum Press, New York, 1989; Michalek, S. M. et al., "Liposomes as Oral Adjuvants," *Curr. Top. Microbiol. Immunol.* 146:51–58 (1989)), which references are hereby entirely incorporated by reference. The active ingredient may be present both in the aqueous layer and in the lipidic layer, inside or outside, or, in any event, in the non-homogeneous system generally known as a liposomic suspension.

The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

Having now generally described the invention, the same will be more readily understood through reference to the following examples which are provided by way of illustration, and are not intended to be limiting of the present invention, unless specified.

EXAMPLE I

HYPERICIN TREATMENT PROTECTS VIRUS PARTICLES FROM DETERGENTS

Following treatment of retroviral particles with hypericin, the virion becomes more resistant to disruption with non-ionic detergents such as 1% aqueous solutions of Triton X-100. Thus it is much more difficult to measure reverse transcriptase from virus treated with hypericin prior to exposure to detergent than with virus first disrupted with detergent and then incubated with hypericin. Since hypericin has no effect on reverse transcriptase enzymatic activity in the assay conditions used (see FIG. 2) this result is presumed to be due to the failure of the enzyme to be released into the assay solution from the capsid structures of the virions because of hypericin's action.

The effects on virion-encapsulated enzyme are presumed to be due to the failure of the capsids, within which the virus is sequestered, to be disrupted after hypericin treatment.

EXAMPLE II

HYPERICIN TREATMENT ABROGATES THE INFECTIVITY OF RETROVIRUS

Hypericin can effectively inactivate retroviral particles rendering them non infectious. As demonstrated in Table 3, HIV infectivity titers are diminished by 3–4 logs after treatment with hypericin.

TABLE 3

Hypericin Reduces Infectivity and Reverse Transcriptase Activity of HIV Infecting CEM × 14 Cells

| Expt | Hypericin (μg/ml) | INHIBITION ($Log_10$ Reduction) RT | INFECTIVITY |
|---|---|---|---|
| 1 | 25 | 1.72 | 4.75 |
| | 10 | 0.60 | 4.00 |
| 2 | 10 | | 4.75 |
| | 5 | | 4.25 |
| | 2 | | 3.75 |
| | 1 | | 0 |

In these experiments infectivity was monitored by HIV-induced destruction of CEM ×174 after these cultures were infected with increasing dilutions of hypericin-treated virus. For Experiment 2, virus was incubated overnight with hypericin at 4° C.. RT: reverse transcriptase activity.

EXAMPLE III

VACCINATION WITH HYPERICIN-INACTIVATED VIRUS

Synthetic hypericin prepared from emodin was solubilized in 0.5% aqueous benzyl alcohol and administered to a concentrated stock of Friend virus estimated to contain greater than $10^4$ virus focus forming units at final hypericin concentrations of 1 μg/ml and 5 μg/ml. The mixture was incubated on ice for one hour. A control preparation was incubated in parallel in the absence of the compound. Additional experimental groups were exposed to light from a 200 watt visible light halogen source in the presence of equivalent hypericin concentrations for 1×30 seconds and 2×30 seconds respectively. Light can enhance the antiviral activity of hypericin (for example, see FIG. 5). However, as shown in FIGS. 6 and 7, increased exposure to light did not enhance the ability of hypericin to inactivate FV (see FIG. 7).

The treated virus was diluted in phosphate buffered saline (PBS) to final dilutions of 1:500 and of 1:2000. The diluted treated and control virus preparations were injected intraperitoneally into BALB/c mice (3 mice per group). A single mouse from each group was sacrificed on day 11 for assessment of spleen size in order to determine the degree of FLV inactivation by hypericin. It is apparent that extracorporeal hypericin treatment of FLV significantly reduced the ability of the virus to induce splenomegaly (FIG. 6).

On day 21, the immunized animals and a new set of unimmunized controls were challenged with live FLV (1:2000 dilution of the original concentrated virus stock). The animals were sacrificed 15 days later and their disease status assessed by spleen weight. A single intraperitoneal administration of a FLV exposed to hypericin at 5 µg/ml for one hour was sufficient to elicit protection from subsequent infection by a challenge with live unattenuated virus. This protection was in a range of approximately 80–90% inhibition of splenomegaly 15 days post-virus inoculation as compared to splenomegaly in unimmunized animals (FIG. 7).

In another experiment, a comparison was made of one, two or three immunizations with hypericin-treated FLV. The results appear in FIG. 8. The virus stock was treated with 5 µg/ml hypericin for 1 hr as described above. The animals receiving 3 immunizations (at the 5 different virus dilutions shown) were immunized on day 0, 21 and 35, and were challenged with live virus on day 42. The group getting 2 immunizations were injected on day 14 and 35 and challenged on day 42. The 1 immunization group was injected on day 21 and challenged on day 42. The splenomegaly resulting from this live virus challenge was then assessed 14 days after challenge and compared to two control groups: negative controls were mice challenged with PBS; positive controls were unimmunized mice challenged with live virus. The results are expressed as % inhibition of FLV-induced splenomegaly (FIG. 8). Three immunizations were more effective for all virus concentrations. Hypericin-treated FLV was shown to be highly effective as a vaccine even at a dilution of 1:2×10$^6$; at this and at 1:2×10$^5$ dilutions, a single immunization was very effective.

EXAMPLE IV

TIME-COURSE OF HYPERICIN TREATMENT FOR IMMUNOGENIC VIRUS

An experiment was performed in which FLV was incubated with 5 µg/ml hypericin for 1, 2, 4 or 6 hours prior to the use of the FLV as a vaccine for inducing protection to subsequent live virus challenge. Following hypericin treatment, the virus was injected intraperitoneally into Balb/c mice. On day 21, mice were challenged with live virus, and splenomegaly assayed 15 days later. The results are summarized in Table 4.

TABLE 4

| Treatment | Hypericin Treatment (hrs) | Spleen Weight (mg) |
|---|---|---|
| PBS | — | 0.135 |
| FLV (1/5000) | — | 1.22, 1.36, 1.29 |
| FLV + hypericin | 1 | 0.26, 1.48, 0.28 |
|  | 2 | 0.39, 0.30, 1.41 |
|  | 4 | 0.83, 0.84, 0.90 |
|  | 6 | 1.41, 1.54, 1.40 |

Spleen weights for individual animals are shown.

These results indicate that immunogenicity of the virus preparation is optimal after 1 or 2 hours of hypericin treatment. Continued treatment for 4 or 6 hours results in poorer immunogenicity, presumably due to degradation of antigenic determinants.

EXAMPLE V

COMPARISON OF VIRUS-INACTIVATING AND IMMUNOGENICITY-ENHANCING PROPERTIES OF HYPERICIN AND ROSE BENGAL

Figure 9:
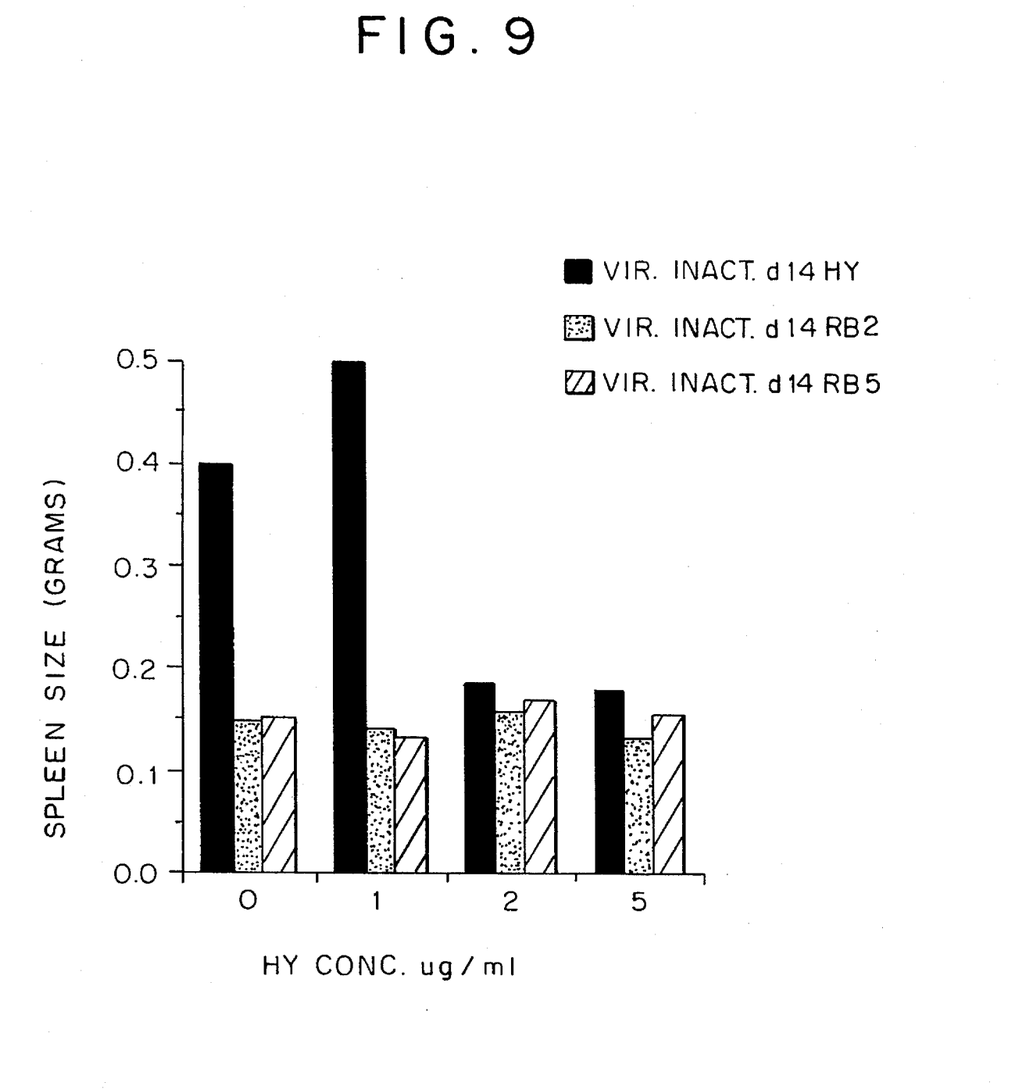
FIG. 9 is a graph showing the inactivation of Friend virus by Hypericin, Rose Bengal and combinations thereof. Friend virus was diluted 1:2000 in PBS and incubated with no hypericin or concentrations of hypericin of 1, 2, or 5 mg/ml alone, or in combination with Rose Bengal (RB) at concentrations of 2 and 5 mg/ml for 1 hour on ice. The treated virus preparations were injected into BALB/C mice. On day 14, 1 mouse from each group was sacrificed and analyzed for spleen weight.
Figure 10:
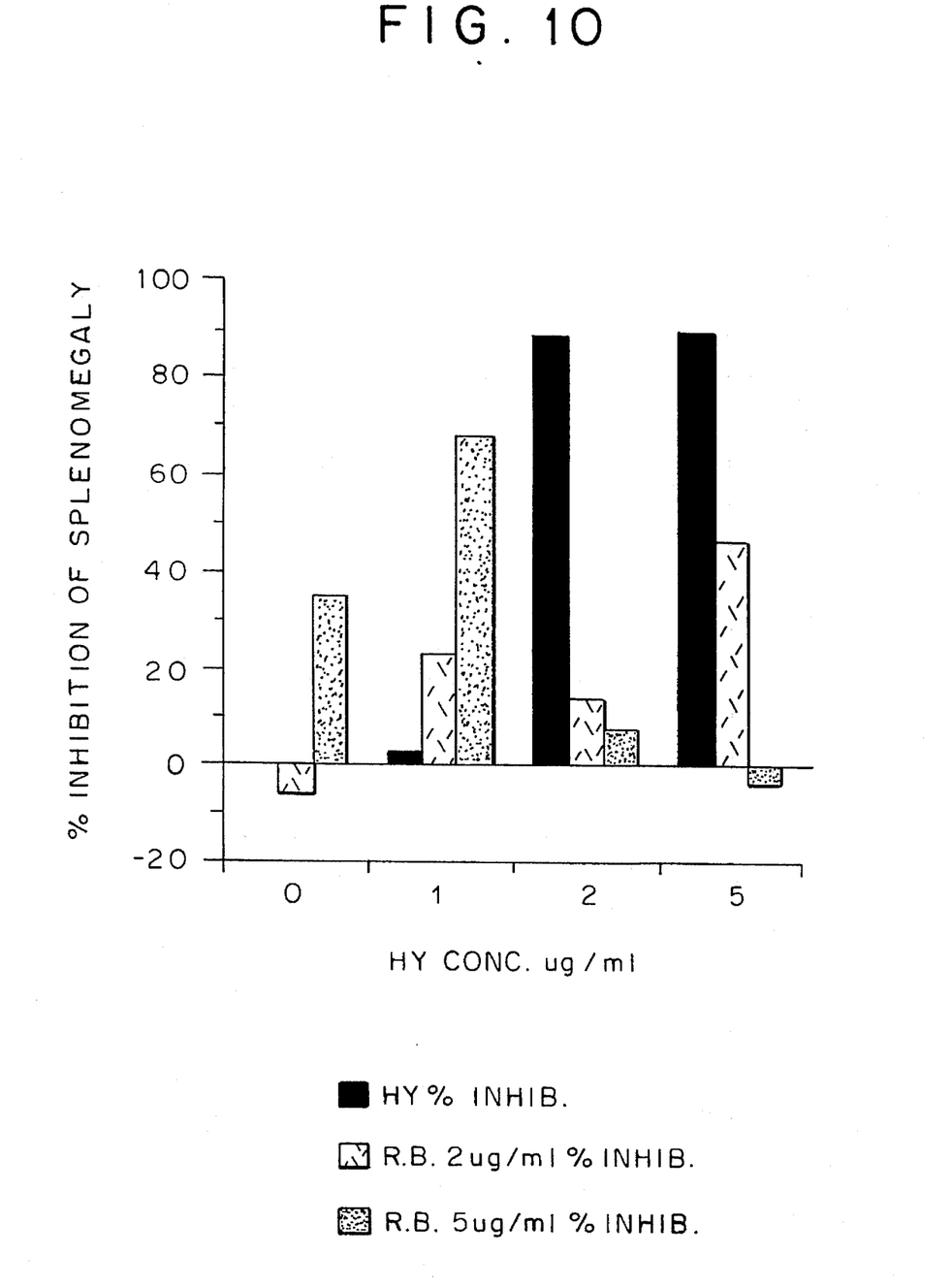
FIG. 10 is a graph showing the protective effect of the inactivated virus preparations described in FIG. 9. On day 21 after administration of the treated virus preparation, all animals were challenged with live Friend virus. Also included were control groups of mice injected with live Friend virus, and mice injected with PBS only. After 15 days, all mice were sacrificed and their spleens weighed as a measure of protection.

FIGS. 9 and 10 show the results of a study in which Friend virus was treated with hypericin, Rose Bengal or combinations of hypericin and Rose Bengal at different concentrations and ratios. The virus treated in this manner was injected into BALB/C mice. FIG. 9 shows an experiment in which Friend virus-induced splenomegaly was assayed as a measure of virus inactivation by these agents. Lack of, or suppression of, splenomegaly serves as an index of the degrees of virus inactivation. The results (FIG. 9) showed that treatment of Friend virus with hypericin at concentrations of 2–5 mg/ml, with Rose Bengal at 2–5 mg/ml, and with combinations thereof, effectively suppressed virus-induced splenomegaly. This proves that virus inactivation by both agents, alone and in combination, was effective.

Another experiment was performed to test whether mice treated with inactivated virus were protected from challenge by live virus, to see whether the inactivated virus preparations demonstrated in FIG. 9 were also immunogenic. In this experiment, inhibition of splenomegaly served as the measure of protection resulting from immunogenicity of the virus preparations. The results shown in FIG. 10 demonstrate that the inactivated preparations giving the greatest degree of protection were those inactivated with hypericin alone. Rose-Bengal treatment alone showed lower levels of protection. In fact, combinations of Rose Bengal with active concentrations of hypericin led to diminution or abrogation of the protective properties of the hypericin-treated virus.

These findings indicate that the property of producing excited oxygen species, shared by hypericin and Rose Bengal, while contributing to virus inactivation, is not sufficient, per se, for enhancing immunogenicity. These findings therefore emphasize the unique and unexpected properties of hypericin in inactivating retroviruses while resulting in a high level of immunogenicity of the viral preparation.

EXAMPLE VI

At the beginning of month one, four naturally occurring warts on the left foot and one on the right foot of a human subject were treated topically with hypericin formulated in basic eye ointment. Small amounts were applied once daily in the morning on each affected site for 10 days.

Significant regressions in wart size were observed which were most noticeable approximately four weeks after the beginning of treatments.

Four weeks after treatment three of the foci on the left foot, which were initially approximately one millimeter in diameter, completely disappeared. One focus, which was approximately 2 mm. in diameter and protruded to approximately one mm. above the surface of the skin, had become flat. The warts on the right foot that were approximately 2.5 mm in diameter also showed a significant regression and completely disappeared two months later.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A method for treating a papilloma virus infection in a subject, comprising topically administering a papilloma virus inhibiting effective amount of hypericin.

2. A method according to claim 1, wherein said papilloma virus is selected from the group consisting of a papilloma virus capable of causing benign warts and a papilloma virus capable of causing a malignancy.

3. A method according to claim 2, wherein said papilloma virus is a benign wart causing virus.

4. A method according to claim 3, wherein said papilloma virus is selected from HPV-1, HPV-2, HPV-6 or HPV-11.

5. A method according to claim 2, wherein said papilloma virus is capable of causing a malignancy.

6. A method according to claim 5, wherein said papilloma virus is selected from HPV-16 or HPV-18.

* * * * *